(12) United States Patent
Smith et al.

(10) Patent No.: US 7,859,682 B2
(45) Date of Patent: Dec. 28, 2010

(54) OPTICAL INTERFERENCE APPARATUS

(75) Inventors: David Steven Smith, Orpington (GB); Simon Richard Hattersley, Bickley (GB); Andrew Gilkes, Orpington (GB)

(73) Assignee: Michelson Diagnostics Limited, Maidstone, Kent (GB)

( * ) Notice: Subject to any disclaimer, the term of this patent is extended or adjusted under 35 U.S.C. 154(b) by 433 days.

(21) Appl. No.: 11/667,924

(22) PCT Filed: Nov. 4, 2005

(86) PCT No.: PCT/GB2005/050196
§ 371 (c)(1),
(2), (4) Date: Oct. 16, 2007

(87) PCT Pub. No.: WO2006/054116
PCT Pub. Date: May 26, 2006

(65) Prior Publication Data
US 2008/0192236 A1      Aug. 14, 2008

(30) Foreign Application Priority Data
Nov. 18, 2004   (GB)   .................................. 0425419.9

(51) Int. Cl.
*G01B 9/02* (2006.01)
(52) U.S. Cl. ..................................................... 356/497
(58) Field of Classification Search ................. 356/479, 356/497
See application file for complete search history.

(56) References Cited

U.S. PATENT DOCUMENTS

| | | | | |
|---|---|---|---|---|
| 3,899,253 A | * | 8/1975 | Overhoff | 356/497 |
| 4,105,335 A | * | 8/1978 | Tanaka et al. | 356/492 |
| 4,487,478 A | * | 12/1984 | Jackson | 359/601 |
| 4,743,114 A | * | 5/1988 | Crane, Jr. | 356/454 |
| 4,768,182 A | * | 8/1988 | Hatfield | 369/112.29 |
| 5,040,872 A | * | 8/1991 | Steinle | 359/638 |
| 5,218,426 A | * | 6/1993 | Hall et al. | 356/517 |
| 5,671,047 A | * | 9/1997 | Curbelo | 356/452 |
| 6,028,706 A | * | 2/2000 | Shirasaki et al. | 359/577 |
| 6,801,299 B2 | * | 10/2004 | Kremer et al. | 355/67 |
| 6,894,789 B2 | * | 5/2005 | Le-Gall et al. | 356/519 |
| 7,002,696 B1 | * | 2/2006 | Miron | 356/519 |
| 7,292,383 B2 | * | 11/2007 | Verma et al. | 359/261 |
| 7,508,582 B2 | * | 3/2009 | Lauer | 359/368 |
| 7,555,024 B2 | * | 6/2009 | Ishaaya et al. | 372/29.023 |
| 2003/0142934 A1 | | 7/2003 | Pan et al. | |
| 2006/0192975 A1 | * | 8/2006 | Sato et al. | 356/497 |
| 2007/0076223 A1 | * | 4/2007 | Podoleanu et al. | 356/511 |
| 2007/0217009 A1 | * | 9/2007 | Richter | 359/487 |
| 2008/0192236 A1 | * | 8/2008 | Smith et al. | 356/73 |

FOREIGN PATENT DOCUMENTS

| | | |
|---|---|---|
| WO | 02/04929 A2 | 1/2002 |
| WO | 2005/033624 A1 | 4/2005 |

\* cited by examiner

*Primary Examiner*—Hwa S. A Lee
(74) *Attorney, Agent, or Firm*—Seed IP Law Group PLLC

(57) ABSTRACT

An optical interference apparatus for carrying out Fourier domain optical coherence tomography. Multiple beams are provided and respective interferograms are recorded simultaneously for a plurality of different focal depths within a substance to be examined. Combined images are derived from the interferograms for a plurality of different focal depths, whereby a single image may be constructed with an increased depth of field. The axial spacing of the foci is calculated to take into account the Rayleigh range of the focal waist in the substance to be examined.

26 Claims, 13 Drawing Sheets

OPTICAL INTERFERENCE APPARATUS

TECHNICAL FIELD

The present disclosure relates to an interference apparatus and method, particularly an optical coherence tomography apparatus and method and a probe for use therein. We will describe an optical probe and associated methods for use with an imaging technique known as optical coherence tomography (OCT).

In one example arrangement, the optical probe may be used in any location which can be reached by a rigid endoscope (or borescope). Potential applications include medical examinations such as colposcopy (cervical cancer screening) and laparoscopy (e.g., in diagnosis and treatment of endometriosis). In another example arrangement, the optical probe may be used in more accessible locations which do not require an endoscope. Potential applications include dermatology (e.g., in skin cancer diagnosis).

BACKGROUND INFORMATION

Internal medical examinations are typically carried out by using an endoscope in which the eye or a CCD camera images the view relayed from the distal end of a shaft of the probe. In a flexible endoscope, the image may be relayed using a coherent fiber bundle containing thousands of individual fibers; in a rigid probe or borescope, the image may be relayed via a system of lenses or rods. Effectively this gives a view of the surface of the relevant medical target, but to see changes in the structure below the surface, it is desirable to be able to obtain a cross-sectional image from within the bulk of the tissue. This is the capability which OCT can provide. Variants of OCT have been described which can extract additional information, such as blood flow velocity (Doppler), or alignment of muscle fiber (polarization).

OCT may be used in the visible part of the spectrum for retinal examination, but to obtain reasonable penetration depth in other, more strongly scattering, tissues it is necessary to move to infrared wavelengths.

OCT is based on the use of interferometry, where light in the measurement arm of an interferometer is passed to the object to be examined and a portion is scattered back to the interferometer. Light in the reference arm is passed to a mirror at a known distance and a reference beam is reflected back. The scattered measurement beam and the reflected reference beam are combined, and the interference between these two beams is detected and used to provide data about the examined object.

Thus optical coherence tomography uses interferometry and the coherence properties of light to obtain depth-resolved images within a scattering medium, providing penetration and resolution which cannot be achieved with confocal microscopy alone. Clinically useful cross-sectional images of the retina and epithelial tissues have been obtained to a depth of 2-3 mm.

There are three main types of OCT which can be categorized as follows:

Time domain OCT; this uses a low coherence source and scans axially (in depth) by altering the reference path length of the interferometer.

Spectral domain OCT; this uses a wide spectrum (i.e., low coherence) source, a stationary interferometer and a spectrometer. The spectrum of the interferogram is examined by the spectrometer and the axial response is obtained as the Fourier transform of the spectrum of the light at the output of the interferometer.

Frequency domain OCT; this uses a swept-frequency narrow spectrum source and a stationary interferometer. The axial response is obtained as the Fourier transform of the time-varying intensity of the light at the output of the interferometer.

We shall use the expression "Fourier domain" to cover both spectral domain and frequency domain.

Time domain OCT (the original, and currently the most prevalent, type) is limited in acquisition speed by the need for mechanical depth scanning, and has relatively poor signal-to-noise performance.

Fourier domain OCT (spectral or frequency domain) enables more rapid capture of high-resolution images without sacrificing sensitivity. The time for each axial scan ("A-scan" in ultrasound scanning terminology) is critical in medical in-vivo applications because of the need for the patient to stay still for the time that it takes to build up successive A-scans into a cross-sectional image ("B-scan").

However, time domain OCT has one significant advantage: it is easy to combine dynamic focal adjustment in step with the mechanical time-delay scan, giving the optimum spot size at the depth which is being probed. In contrast, Fourier domain OCT acquires information from the whole depth at the same time, so it is not possible to dynamically adjust focus for best lateral resolution.

There are three main difficulties in providing a practical arrangement of an OCT probe in which the conflicting optical and medical requirements are resolved.

Firstly, there are difficulties in obtaining an image which is suitably in focus over the depth of the (A scan) image.

Secondly, to provide a B-scan image it is necessary to scan laterally across the surface. Designs exist for endoscopic probes which incorporate a miniature scanning device in the probe shaft tip, for instance using electro-magnetic coils to move the end of an optical fiber. This approach has the disadvantage of placing moving parts, and the power to drive them, inside the patient's body, and may increase the difficulty of sterilizing the equipment.

Thirdly, it is desirable to be able to provide a normal, full field, endoscope viewing channel at the same time.

Through this specification we will refer to "optical", "light" and such terms. It will be understood, however that such terms refer to radiation of infra-red, visible or ultra-violet wavelengths as appropriate.

BRIEF SUMMARY

In order to deal with the first problem, according to a first aspect, the present disclosure provides an optical interference apparatus and method. For example, but not restricted to an optical coherence tomography apparatus and method in which interferograms are recorded simultaneously for a plurality of different focal depths within the substance to be examined.

Thus, each interferogram provides an A-scan image which is substantially sharp focus over a limited depth range (the depth of focus, also known as the Rayleigh range), but by combining these images for a plurality of different focal depths, a single A-scan image may be constructed with an increased depth of field.

The interferometer passes a measurement beam to the substance to be examined and the apparatus may provide a relevant measurement beam for each different focal depth. If the light is provided by a common source (as is most convenient)—which common source may be a laser—then optical means (such as an amplitude beam-splitter) may be provided to generate a plurality of beams. Different optical components (e.g., refractive elements) are then used in the path of each beam to bring them to different foci.

The depth of focus of each measurement beam is proportional to the square of the diameter of the measurement beam (i.e., proportional to the spot area). Therefore we can halve the spot size (double the lateral resolution) by providing four spots instead of one.

The axial spacing of the foci is calculated to take into account the wavelength of light in the target (which is smaller than that in air by the factor of the refractive index for the relevant wavelength range).

To perform a B scan, it is necessary to relatively scan the beams and the surface being examined, and thus a scan means is provided. Usually a scan means is provided for scanning the beams along a line across the surface of the substance being examined. For a convenient optical design, it is desirable for the plurality of beams to be spaced along the scan line to a small extent. This leads to the information for different depth ranges at a given location arriving at slightly different times during the lateral scan, rather than simultaneously, an effect which has to be compensated for in assembling the combined image.

In order to deal with the second problem, according to a second aspect, the present disclosure provides an optical probe (which may be used with coherence tomography apparatus or other optical arrangements, for example, a viewing endoscope in which an image is transmitted by the probe to a remote viewing lens or to a camera) in which a scanner (e.g., a small rotating or oscillating mirror scanner), is provided at a proximal end of a probe, and optical components are provided within the probe to optically relay the scan to and from a distal end of the probe.

In such embodiments, no moving parts are placed at the distal end of the probe shaft and hence, where it is used for internal medical examination, no moving parts are within the patient.

In some embodiments, the probe may comprise a probe shaft, and a handle at the proximal end of the probe shaft, and a scanner mounted within the handle. The probe shaft may be detachable from the handle for cleaning (the probe shaft would normally be used within a disposable sheath however). Note that, in some embodiments, the shaft may be constrained to a specific orientation, so that any internal baffles which may be fitted within the shaft, or lens tilts to eliminate reflections, will align correctly with the scan direction. Because the scanner is not within the probe shaft itself, different variants of probe shaft may conveniently be provided, mating to the common handle, allowing different lengths of probe shaft, and probe shafts with angled views. If the length of the optical measurement path through the probe shaft is altered, a corresponding compensation in the reference path will be required.

In order to deal with the third problem, according to a third aspect, the present disclosure provides an interference apparatus and method such as an optical coherence tomography apparatus for examining a substance, said apparatus including a viewing apparatus, an interference apparatus, a probe shaft including relay optical components in which viewing (illumination and imaging) is provided through the same relay optical components as are used for the interferometry (e.g., OCT), means to pass an interferometer (e.g., OCT) beam along the probe shaft to the distal end thereof to the substance to be examined and to pass the scattered interferometer (e.g., OCT) beam back along the probe shaft to the interference apparatus, a visible light source (such as a white light source), means to pass the visible light from the visible light source along the probe shaft to the distal end thereof to illuminate the substance to be examined, for example uniformly, and to pass an image thereof back along the probe shaft to an image detector of the viewing apparatus, means to separate the returning image from the outgoing visible light, and a beam-splitter positioned between the proximal end of the probe shaft, and the viewing apparatus and interference apparatus respectively, to separate the interferometer beams (in both directions) from the visible light beams (in both directions) whereby the same part of the substance may be viewed using the visible light and examined using the interference beams at the same time.

The beam-splitter is, in some embodiments, a spectral beam-splitter.

In some embodiments, a scanner is provided to scan the OCT beam across the substance to be examined and in this case the beam-splitter is, in one example, provided between the scanner and the probe shaft, so that in this case, the scanner is considered to be part of the interference apparatus.

The visible light source is, in some embodiments, an LED source to provide white light illumination, and the imaging detector is, in some embodiments, a color CCD camera to receive the reflected image of the surface of the substance being examined.

Such an arrangement allows the clinician to view the surface of tissue, both when the probe is close above it and when the probe is in contact with it. The clinician can use the viewing device to select a particular part of the surface for more detailed in-depth examination by the OCT apparatus, then press the distal end of the probe shaft into contact with that part of the surface while continuing to observe it.

The probe shaft will generally be rigid as this simplifies the optics, but in some circumstances may be at least partly flexible or jointed.

BRIEF DESCRIPTION OF THE SEVERAL VIEWS OF THE DRAWINGS

One or more embodiments of the invention will now be described by way of example and with reference to the accompanying drawings in which.

DETAILED DESCRIPTION

General Description

Figure 1:
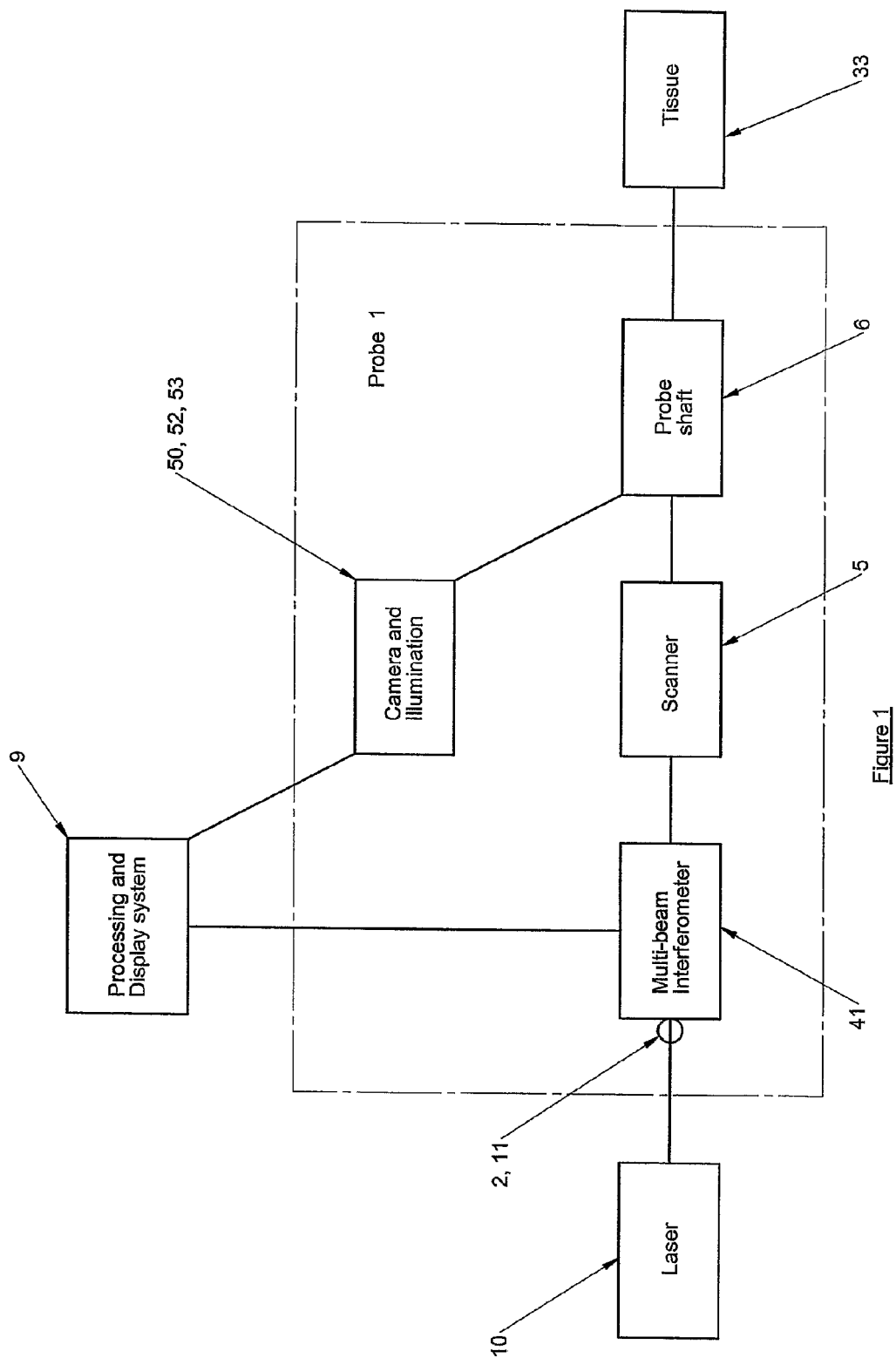
FIG. 1 is a block diagram showing the main components of an optical coherence tomography apparatus according to one illustrated embodiment.

FIG. 1 shows a block diagram of an OCT apparatus indicating a laser 10, provided usually remotely from a probe 1, but in some circumstances within the probe 1. In some embodiments, a laser beam 11 from the laser 10 is passed to the probe, usually through a single-mode optical fiber 2. The laser 10 provides a swept spectrum over a wavelength range of at least 50 nm, within a region of the infra-red where tissue absorption is minimized. A wider spectrum improves the depth resolution. The probe 1 comprises a multi-beam interferometer 41, a scanner 5, a probe shaft 6 and camera with illumination system 50, 52, 53, and other components detailed below. In some embodiments, the processing and display system 9 and tissue under examination 33 are external to the probe 1.

Figure 2:
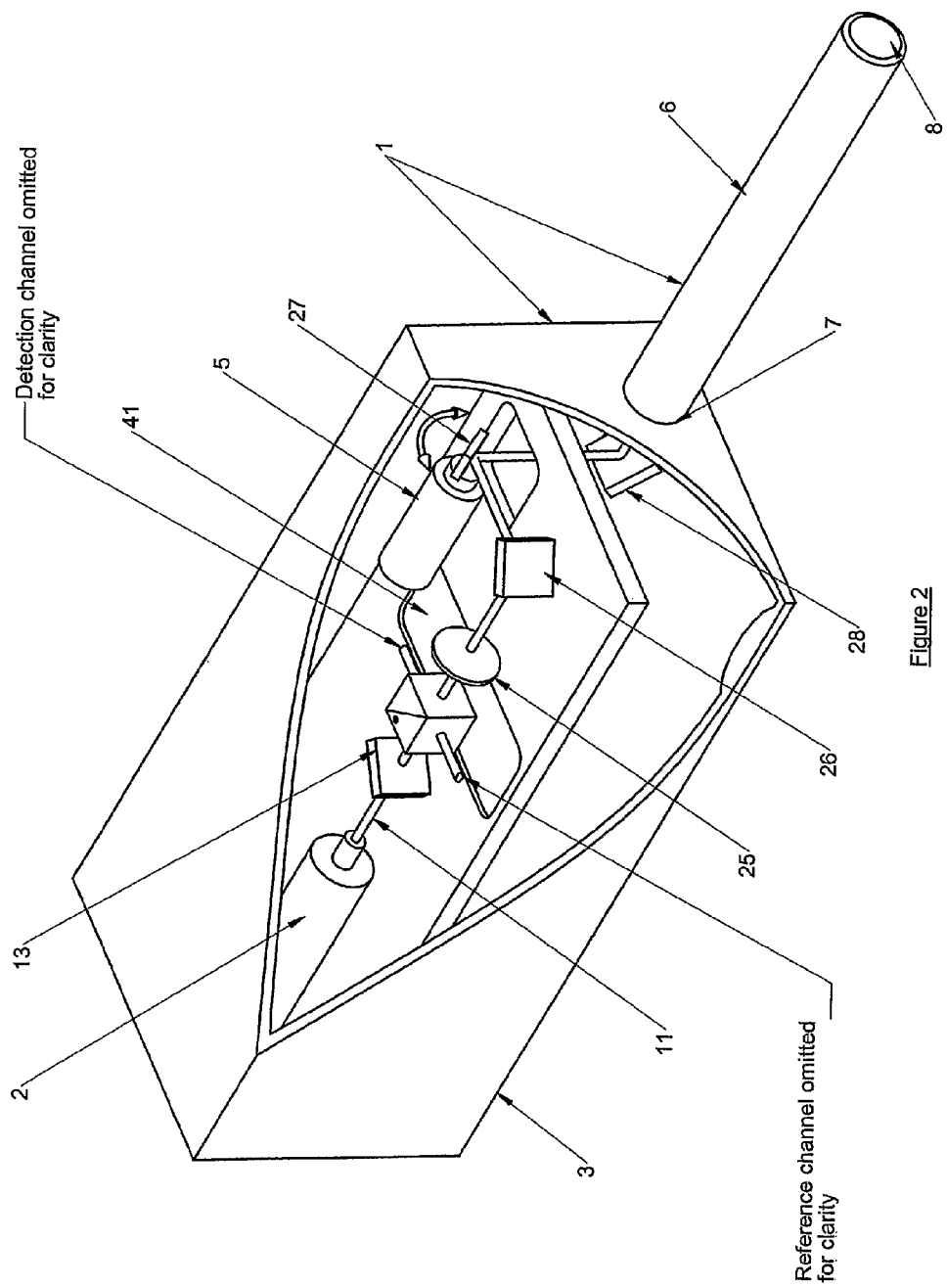
FIG. 2 shows a perspective of the probe with some internal detail according to one illustrated embodiment.

FIG. 2 shows more detail of the probe 1. The probe 1 comprises a handle 3 containing an multi beam interferometer 41 and scanner 5, and a probe shaft 6. The probe 1 is constructed so that the shaft 6 can be detached from the handle 3. The shaft 6 is constrained to a specific orientation, so that an output lens which outputs a multiple beam set and which is tilted by a small angle to eliminate reflections, aligns correctly with the scan direction. Other components described below have been omitted from this diagram for clarity.

For the particular application of imaging the uterine cervix, suitable probe shaft dimensions are approximately 16 mm diameter at the proximal end 7 tapering to 12 mm diameter at the distal end 8 if required, and in the region of 220 mm length. The length of the scan line is made as large as possible, within the constraint of the shaft diameter, and in the described arrangement is 6.4 mm. The cone angle within the tissue is approximately f/8, which gives a depth of focus of about 0.3 mm. One beam of multiple beams used is essentially in focus from about 0 to about 0.3 mm depth, the next beam from about 0.3 mm to about 0.6 mm and so on through to 1.2 mm: the worst-case beam diameter at the tissue under examination (i.e., the width of a spot produced by the beam) is about 10 µm FWHM.

In some embodiments, the distal end 8 of the probe shaft is convex to apply even pressure over the whole front face to the soft tissue under examination, irrespective of small angular departures from the normal onto the surface. Some other internal components including rattle plate 13, lens 25, fold mirror 26, scan mirror 27 and spectral beamsplitter 28 are shown to facilitate orientation.

Optical Description

Figure 3:
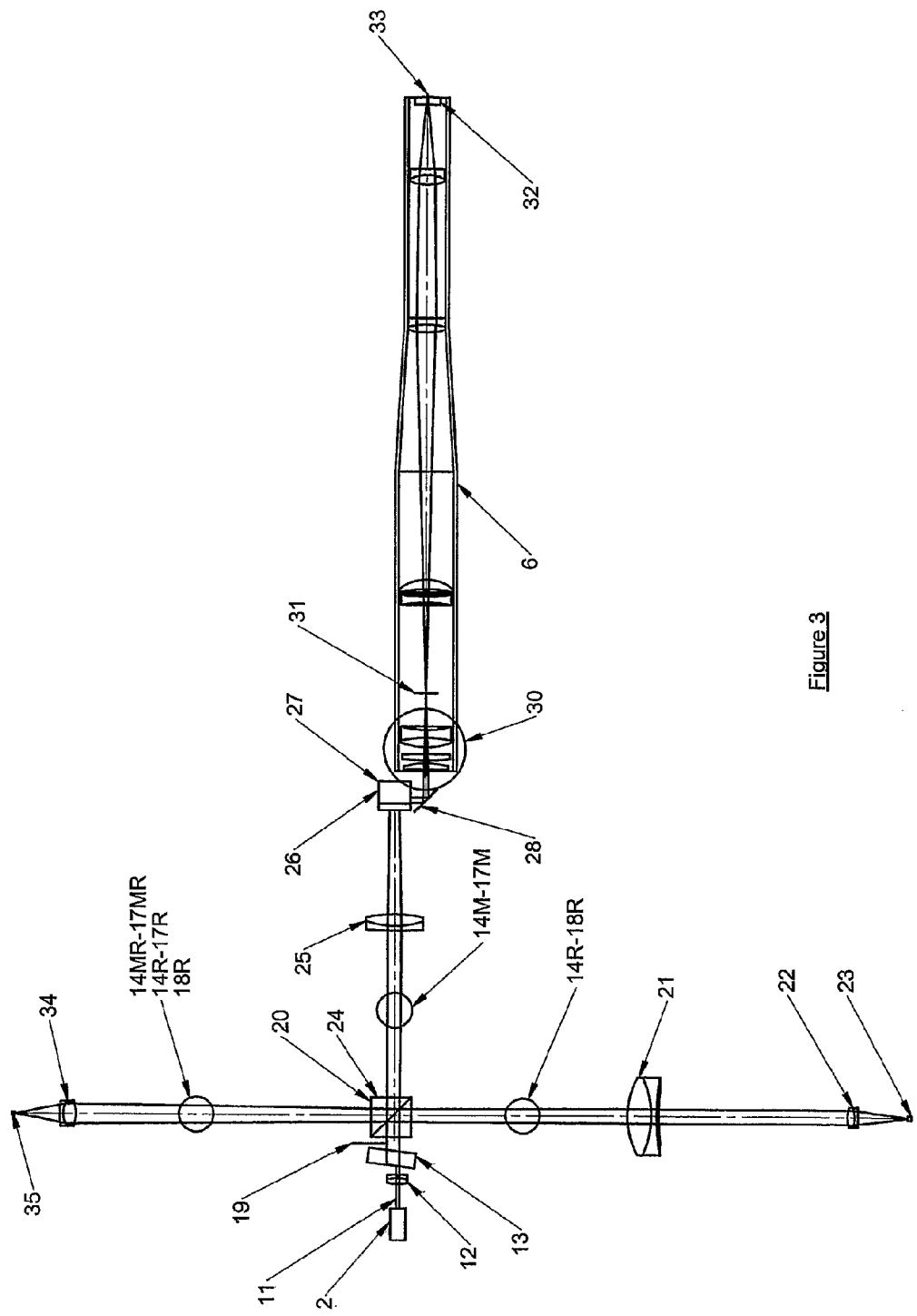
FIG. 3 is an optical diagram of an optical coherence tomography apparatus comprising a four-spot probe used for frequency domain OCT in accordance with one illustrated embodiment (for clarity, some folds of the light paths have been removed).

Referring to FIG. 3, the laser provides an output beam 11, via single mode fiber 2, which is passed to a converging lens 12. After passing through the converging lens, the beam enters the rattle-plate beamsplitter 13. It may be desirable to interpose additional optical components in beam 11 (between the output from the fiber—which may already be collimated—and the rattle-plate) so that the beam diameter can be adjusted, and hence the desired convergence can be produced at the measurement point. The rattle plate 13 splits the beam 11 into a number of weaker beams that are transmitted onwards; the detailed operation of the rattle plate is explained with reference to FIG. 4.

Figure 4:
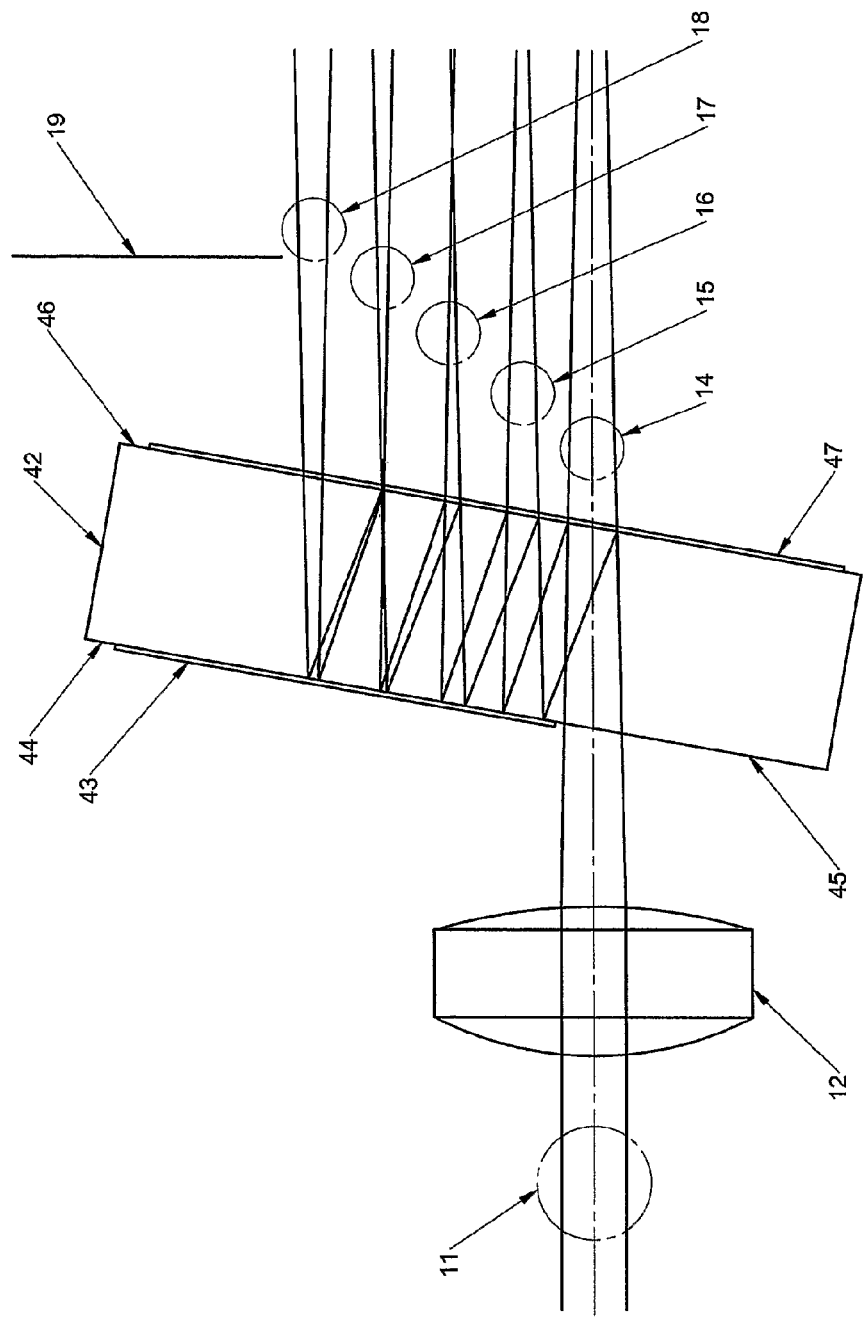
FIG. 4 is a an enlarged axial section of method of multiple beam generation according to one illustrated embodiment.

FIG. 4 is an optical diagram showing the operation of a partially and fully reflecting pair of surfaces in forming a plurality of parallel beams. This arrangement is known as the rattle plate 13. In some embodiments, the apparatus comprises a parallel-sided glass plate 42, which on the entry face 44 has a high efficiency reflective coating to provide a reflective surface over area 43, leaving a non-reflective area 45 which may be either uncoated, or anti-reflection (AR) coated for better performance. The transition between these two areas is sharp. The exit face 46 is coated over the entire surface with a partially reflecting coating to provide a partially reflecting surface 47 such that typically about 8% to about 25% of the incident light is transmitted, and the remainder reflected.

The incoming laser beam 11 passes through the non-reflective area 45 of face 44 (close to the boundary between the reflecting surface 43 and the non-reflective surface 45). Consequently, only a small amount of energy is lost on entry to plate 42 (i.e., the Fresnel reflection if there is no AR coating in this part of the plate, or less if AR coated).

The laser beam 11 propagates through the plate 42, and in this example 13% is transmitted at the partially reflecting surface 47 to provide the first beam 14, and the remainder is reflected back towards the reflecting surface 43.

The plate 42 is tilted from orthogonal to the input beam 11 such that the beam reflected from the partially reflecting surface 47 is directed towards the high-efficiency reflecting surface 43. Consequently the beam is then reflected back (approximately 100% of the energy is reflected) to the partially reflecting surface 47, where a further 13% of the remaining beam power is transmitted to provide the second beam 15. In this way, a series of beams of declining power are emitted from the plate, parallel to each other.

If the input beam 11 at the rattle plate is arranged to be convergent rather than collimated (for example by taking a collimated laser beam and passing it through converging lens 12), then the beams 14, 15 etc leaving the glass plate 42 will focus at different axial positions relative to each other, since each successive beam follows a longer path through the plate 42. The distance between the focal positions will depend upon the thickness, tilt angle and refractive index of the plate 42. Alternatively, the rattle plate assembly may comprise a fully reflecting and partially reflecting surface separated by air, as opposed to glass. Also, the input beam 11 may be divergent rather than convergent with suitable changes to the optical components.

The strongest five beams, 14 to 18, are allowed to propagate onwards, the remainder are blocked by an opaque plate 19.

Returning to FIG. 3, the beams 14 to 18 from the rattle plate 13 are passed to a beam-splitter 20 which divides the beams into measurement beams 14M to 18M and reference beams 14R to 18R. The reference beam 18R is manipulated in the same way as the reference beams 14R to 17R, but it is not used to interfere with a measurement beam, rather it provides compensation for laser amplitude variation.

The reference beams 14R to 18R are reflected by the beamsplitter 20, pass through lenses 21 and 22, reflect at a multi-faceted mirror structure 23 then re-pass through lenses 22 and 21, and re-pass through beamsplitter 20. The multifaceted mirror structure 23 has a reflecting surface for each of the reference beams, the individual reflecting surfaces are set at the foci of the respective beams. It may be advantageous to set the angles of the reflecting surfaces one to the next to ensure that the reference beams 14R to 18R are accurately retro-reflected. Alternatively, the power and position of lenses 21 and 22 may be selected such that the axes of reference beams 14R to 18R are parallel to each other. Note that the reference optical path is shown in the diagram as substantially shorter than measurement optical path. In practice, these paths would be very similar in length, because in a frequency domain OCT system the fringe frequency due to a target reflection is proportional to the path difference. Even if the electronic system could operate with unlimited bandwidth, there would be a constraint on maintaining similar path lengths, since the difference of the path lengths must be less than the coherence length of the laser 10 for interference to occur. Another criterion for good interference between measurement and reference beams is that the convergence and focal positions of the reference beams should match those of the measurement beams at the detectors. To achieve this, additional reflecting or refracting optical components (such as an Offner relay) may be introduced in the reference path to relay the focal points at or near beamsplitter 20 to the multifaceted reflecting surface 23.

The measurement beams 14M to 17M leave beamsplitter 20, and the weakest beam 18M is blocked by an opaque plate 24. They are nominally collimated by lens 25, but there will be a slight difference between the convergence of the four beams since the path length between lenses 12 and 25 is different for each beam. The separation between the two lenses is set so that the average optical path length would result in a collimated beam. The axes of the four beams 14M to 17M now converge towards each other. The beams are reflected at 90° orthogonal to the plane of the diagram at mirror 26, and propagate onwards, with the axes meeting at a scan mirror 27.

The scan mirror 27 is driven to rotate nominally about an axis parallel to the original axis of the beam 11, parallel to the plane of the diagram, scanning the measurement beams 14M to 17M. A further beamsplitter 28 is provided to reflect measurement beams 14M to 17M along a new axis nominally parallel to the original beam axis of beam 11. The beamsplitter plate has a coating to selectively reflect IR radiation such as would be used for beams 14M to 17M, and to transmit visible white light.

A probe shaft 6 is provided. It comprises a metal tube mounting various passive optical components (relay optical components) as will be described hereafter.

The first (entry) lens group 30 in the probe shaft 6 forms a focus at 31 of each of the scanning measurement beams 14M to 17M within the probe shaft; other lenses relay the foci to a focus point just beyond the last lens 32 in the probe shaft, that is, just outside the distal end of the probe shaft. Because the measurement beams 14M to 17M enter the probe shaft with a slightly different divergence from each other, their final focus 14F to 17F outside the probe shaft 6 for the respective beams 14M to 17M as shown in FIG. 5, will be displaced axially relative to each other, allowing optimal signals to be derived from a different tissue depth (the tissue is indicated at 33).

It will be seen that the last lens 32 forms the distal end of the probe shaft. In use, the distal end of the probe shaft formed by the lens 32 will be brought into contact with the medical surface tissue 33 to be examined, optionally through a thin transparent disposable sheath.

Figure 5:
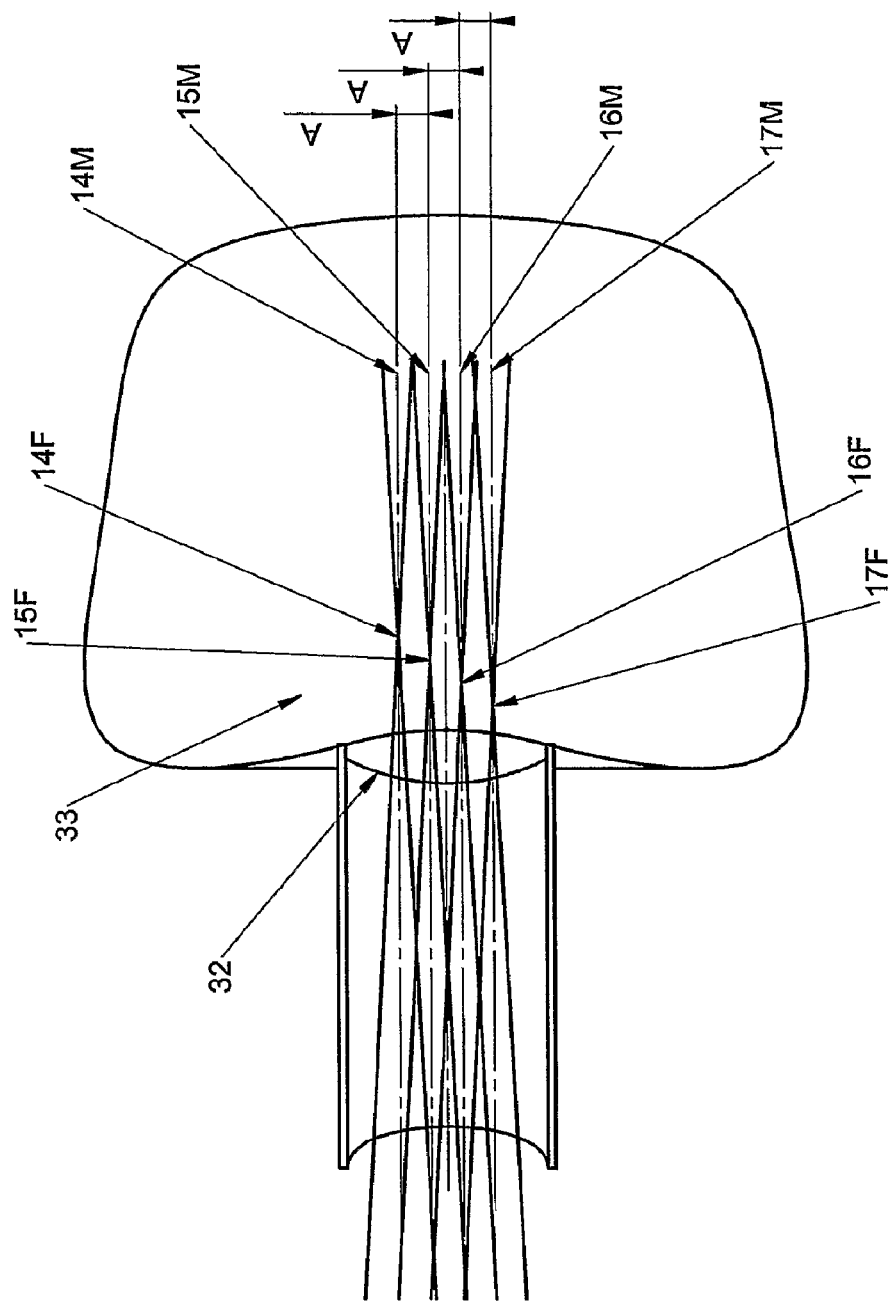
FIG. 5 is an enlarged detail of measurement laser beams at the distal end of a probe, showing both axial and lateral separation of focus according to one illustrated embodiment.

As is shown in FIG. 5, the foci 14F to 17F of the four measurement beams 14M to 17M will fall inside the tissue to be examined. This allows provision of four laser beams which are focussed at different depths, and though each beam rapidly comes out of focus as the depth varies, it is possible to cover all of the depths of tissue of interest within the focal range of one of the four beams. The axial spacing of the four foci is calculated to take into account the Rayleigh range of the focal waist in the tissue to be examined.

Furthermore, because the four beams 14M to 17M strike the scan mirror 27 at slightly different angles, the four foci 14F to 17F outside the probe shaft are also separated along the scan line by a distance indicated at A in FIG. 5. The distance A is small (of the order of 0.2 mm) and so the time between each of the beams scanning across a particular point in the tissue under examination is small (a few percent of the total scan time) and so the tissue under examination should not change between the passage of each beam.

One may have more or less than four beams which have foci at a range of depths within the tissue. It will be noted that the foci of the four beams are displaced both laterally and axially from one to the next.

After scattering from the target tissue, components 14MR to 17MR of the four beams are confocally collected back through the probe shaft. These return beams 14MR to 17MR are de-scanned by the scan mirror 27 and pass back through lens 25.

A part of the each of the beams 14MR to 17MR is reflected by the beam-splitter 20 and combined with the corresponding reference beam 14R to 17R. The combined beams 14MR/14R to 17MR/17R pass through a lens 34 which forms focal points of each of the combined beams at detector 35. It will be seen that the detector plane is tilted to the orthogonal angle of the incident combined beams axes from the normal to accommodate the focal shift originating from the rattle plate 13. Interference between corresponding beams occurs at the surface of the detector 35. The detector 35 will consist of a number of discrete sensitive areas, one for each of the combined beams, and an additional area for the reference beam 18R, which is used as a balance signal.

The beam-splitter 20, reference mirror structure 23, and individual detector sensitive areas 36 to 39, and optical components form a Michelson interferometer 41. The interferometer arrangement allows the use of OCT and in particular the optical components are provided in this embodiment to use frequency domain OCT.

It will be seen that if beamsplitter 20 is a polarizing beamsplitter, and quarter wave-plates are interspersed in both measurement and reference paths such that the measurement beams 14M to 17M, and reference beams 14R to 18R pass and re-pass through the wave-plates, and if an additional analyzing component is added to the combined path so that a common polarizing component of each of the beams is selected, then the assembly will have a modified sensitivity to any polarized properties of the tissue under examination.

Figure 6:
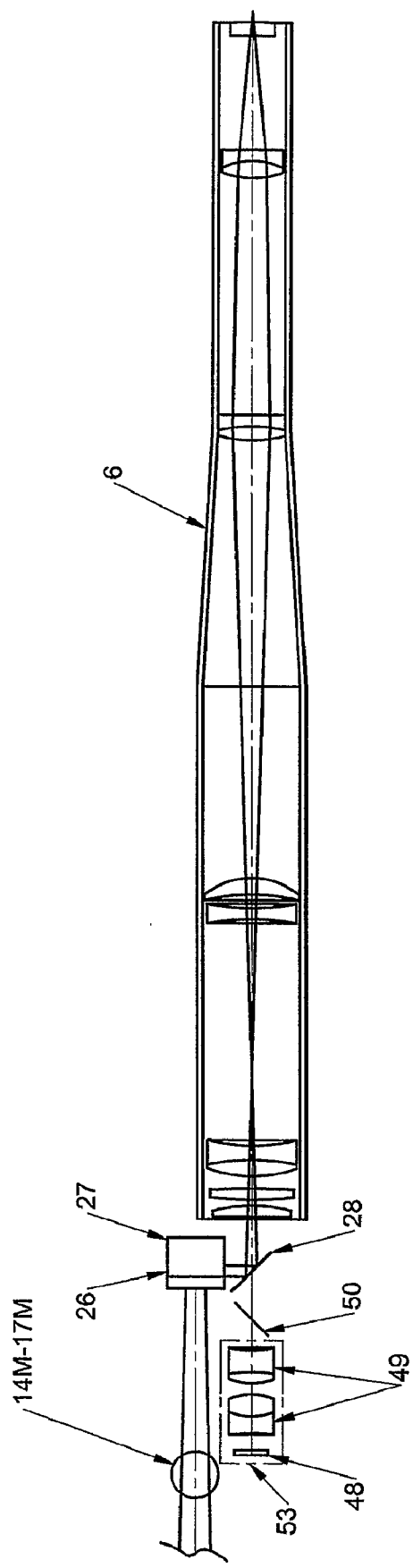
FIG. 6 is an axial section of a probe assembly incorporating viewing optics including a camera and optical components to provide a view of the surface under examination, the figure showing the path of the laser OCT beams according to one illustrated embodiment.
Figure 7:
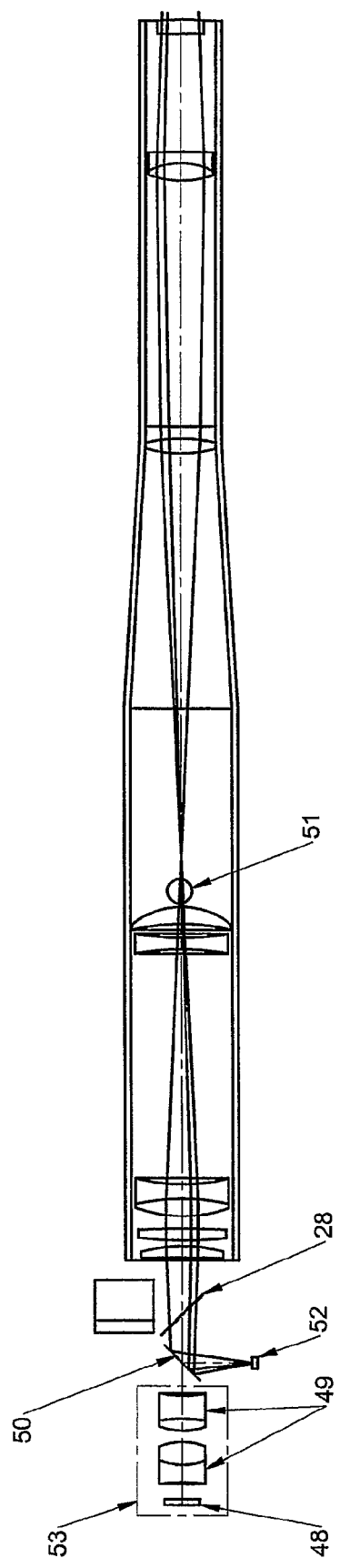
FIG. 7 is an axial section of a probe assembly of FIG. 3 showing the illumination light optical path excluding the laser beams according to one illustrated embodiment.

Additional details are shown in FIGS. 6 and 7 to provide a viewing channel.

In FIG. 6, the path of the OCT laser beams 14M to 17M is shown. The laser beams 14M to 17M are traced from lens 25 (not shown), via mirror 26 onto the scan mirror 27, and through to the tissue at the distal end of the probe shaft 6. A camera chip 48, lens system 49 and illumination beamsplitter plate 50 are also shown.

Figure 8:
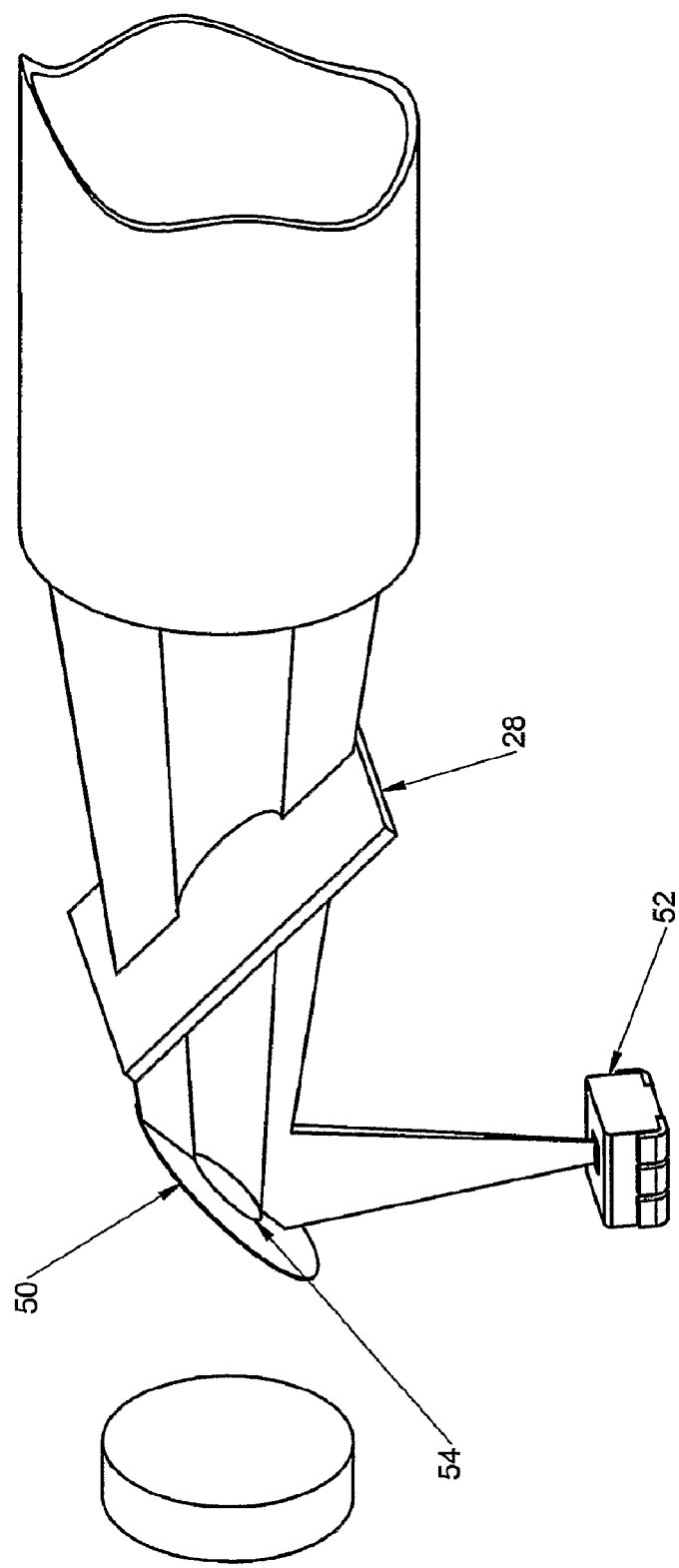
FIG. 8 is an expanded view of a method of mixing the illumination light path with the viewing light path according to one illustrated embodiment.

FIG. 7 shows the same components as FIG. 6 but the illumination beams 51 and white light source 52 are shown, and the OCT laser beams are omitted for clarity. FIG. 8 shows an additional view of the illumination beamsplitter plate 50, which is a reflecting surface with a central aperture. Light from white light source 52 is largely reflected by the illumination beamsplitter plate 50, although those parts of the beam which pass through the central aperture 54 are lost.

Figure 9:
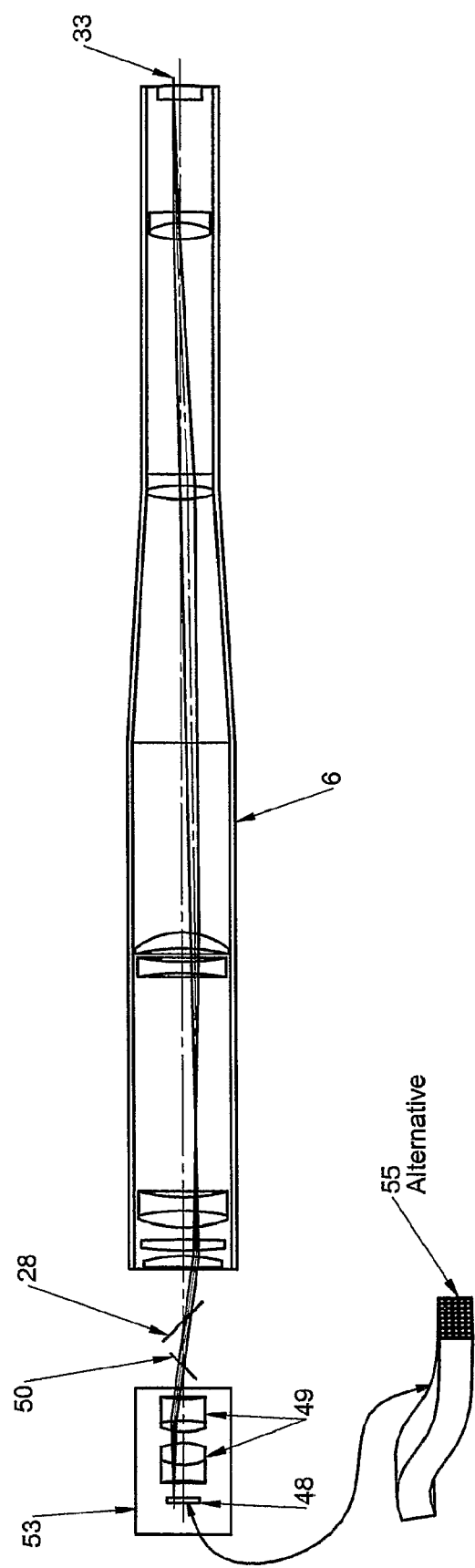
FIG. 9 shows the imaging light path from the distal end of the probe to the camera according to one illustrated embodiment.

The apparatus of FIGS. 6 and 7 includes a spectral beam-splitter 28 which separates OCT laser light from white light. The illumination beam-splitter plate 50 and illumination source 52 are positioned to direct visible light, for example white light, from the illumination light source 52 through the beamsplitter plate 28, and to pass a beam 51 of white light from the source 52 along the optical axis within the probe shaft 6. A white light LED is a suitable illumination source 52 but others are envisaged. Since the tissue surface 33 will be optically scattering, a component part of the returned reflected white light beam 51 will pass through the spectral beam-splitter 28. A smaller component of this returned beam will pass through the aperture 54 in the illumination beam-splitter plate 50 to a camera 53 which includes a CCD detector 48. This is illustrated in FIG. 9.

As is clear from FIGS. 6 and 7, the spectral beam-splitter 28 allows an illuminating beam 51 to be passed to the surface under examination, the illuminating beam being mixed into the viewing channel by beam-splitter 50.

In some embodiments, the entrance pupil 54 of the camera will be at a conjugate point to the reflective surface of the scan mirror 27, and also coincident with aperture of the illumination beamsplitter plate 50.

The camera 53 includes one or more lenses 49 to form an image of a surface to be examined. The camera may be used to examine the surface 33 when it is in contact with the distal end of the probe shaft. Further, if the depth of focus of the camera is sufficient, it may be used when the distal end is spaced from the surface allowing the user to carry out a survey of the surface before selecting a particular part to be examined by OCT.

Referring to FIG. 9, the image is focussed on either the image sensor surface 48 of the camera 53, or in an alternative arrangement, an end surface of a coherent fiber bundle 55 which leads to a remote CCD.

It will be noted that both the viewing optics and the OCT apparatus use the same distal end lens 32 and so the part of the tissue viewed by the camera 53 and the OCT interferometer 41 will be the same. Means may be provided for indicating on the displayed image the position of the OCT B-scan line.

Figure 10:
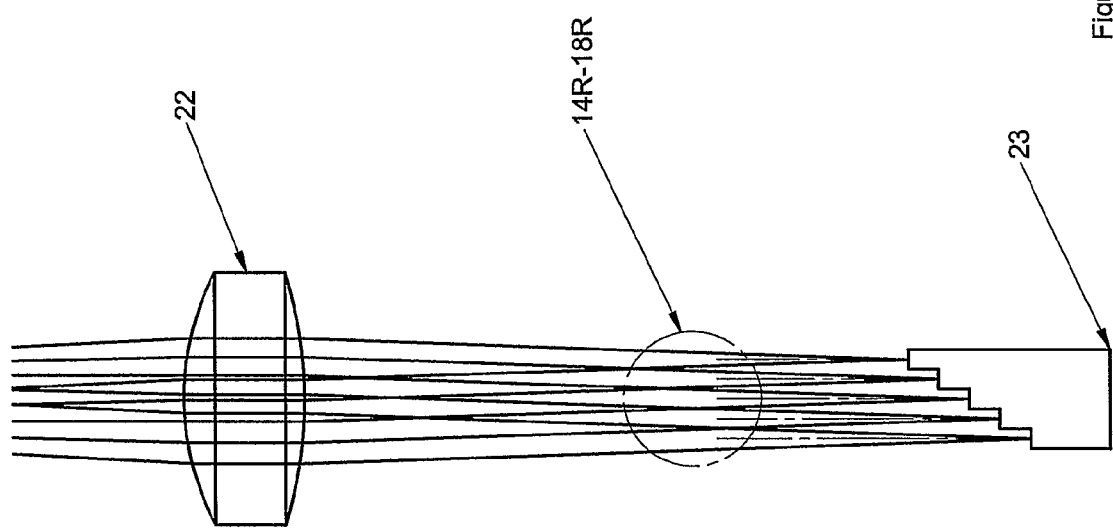
FIG. 10 is an enlarged detail of a multi-facet reference mirror structure according to one illustrated embodiment.
Figure 11:
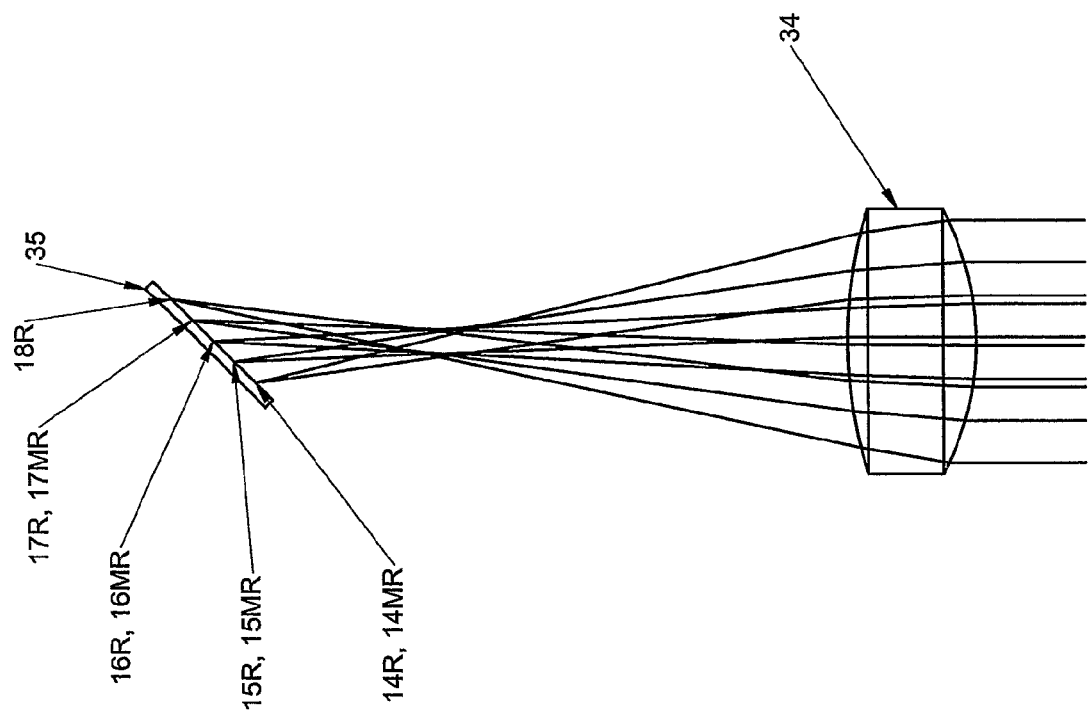
FIG. 11 is an enlarged detail of interfering laser beams and a balance beam forming image foci on the detector plane according to one illustrated embodiment.
Figure 12:
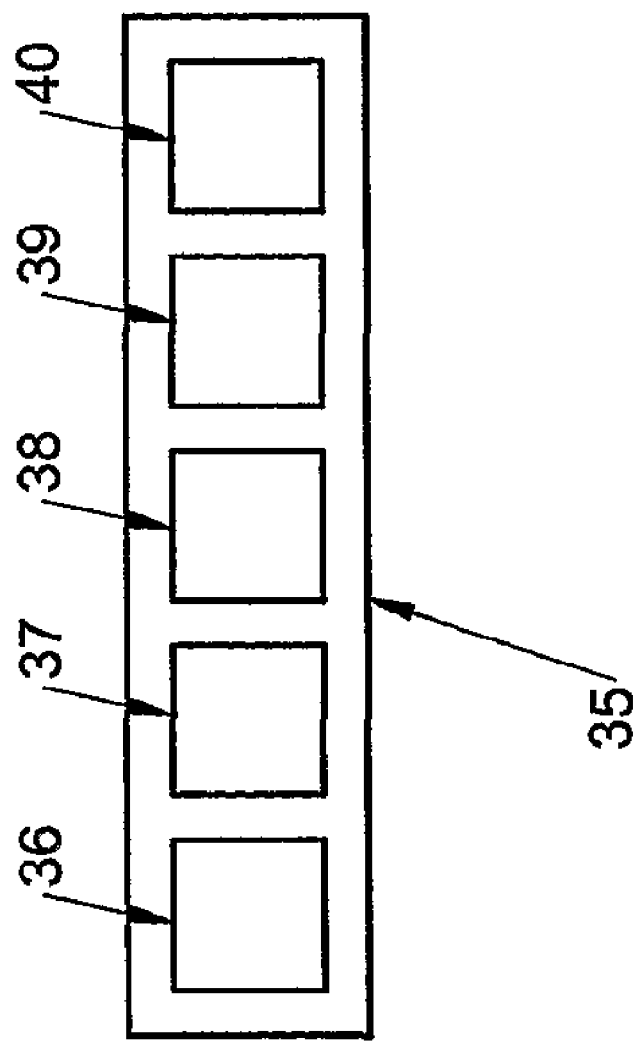
FIG. 12 shows an enlarged detail of sensitive areas on a detector plane according to one illustrated embodiment.

FIG. 10 shows a magnified view of the reference mirror structure 23. FIG. 11 shows the combined beams 14MR/14R to 17MR/17R, and balance beam 18R forming individual foci on the detector surface 35. FIG. 12 shows the arrangement of the sensitive areas on the detector plane, one for each combined beam, and one for the balance beam 18R.

The embodiment so far described uses a single balance beam, and a compensation signal derived from this beam is applied to each of the (four) interference signals electronically. An alternative embodiment is to provide a separate balance beam matched optically to each reference beam; the paired beams are then detected using a balanced detector configuration.

Processing Description

The laser provides a trigger signal to the processing system at the start of each frequency sweep. The processing system digitizes the analogue detector signals and stores the data (typically 1024 points) for the sweep, which provides the information to reconstruct one A-scan. The processing system may capture raw data for many A-scans (covering the entire movement of the scan mirror) before processing into a B-scan image, or alternatively capture and processing of A-scans may be overlapped in time.

An ideal laser source for frequency domain OCT would sweep at a constant rate of optical frequency with time, and provide a constant level of power during the sweep. In this case it would only be necessary to perform a discrete Fourier transform of the raw data (with an appropriate window function, e.g., Hanning) to obtain the A-scan profile.

For practical laser sources, the sweep rate varies across the spectrum, and so does the power. If uncorrected these effects would result in blurred images. Accordingly the raw data is corrected by resampling at unequal intervals using a local cubic interpolation algorithm, and by rescaling by varying factors. The discrete Fourier transform is then performed as above.

The calibration for the above corrections is obtained by using a plain glass block as a target, to generate a single reflection of about 4% of incident power (the scan mirror is stationary, set to the central position, during calibration). The path difference is adjusted to give a suitably large number of fringes (for instance 100 across the scan), and the raw waveform is captured. After removing any residual dc component, the computer accurately determines the position of the fringe zero crossings using a local cubic interpolation algorithm, and hence obtains the required array of resampling positions. It also determines the envelope of the fringes, and hence obtains the required array of rescaling values. When the system is correctly calibrated, the glass block gives a sharp single peak in the A-scan.

Figure 13:
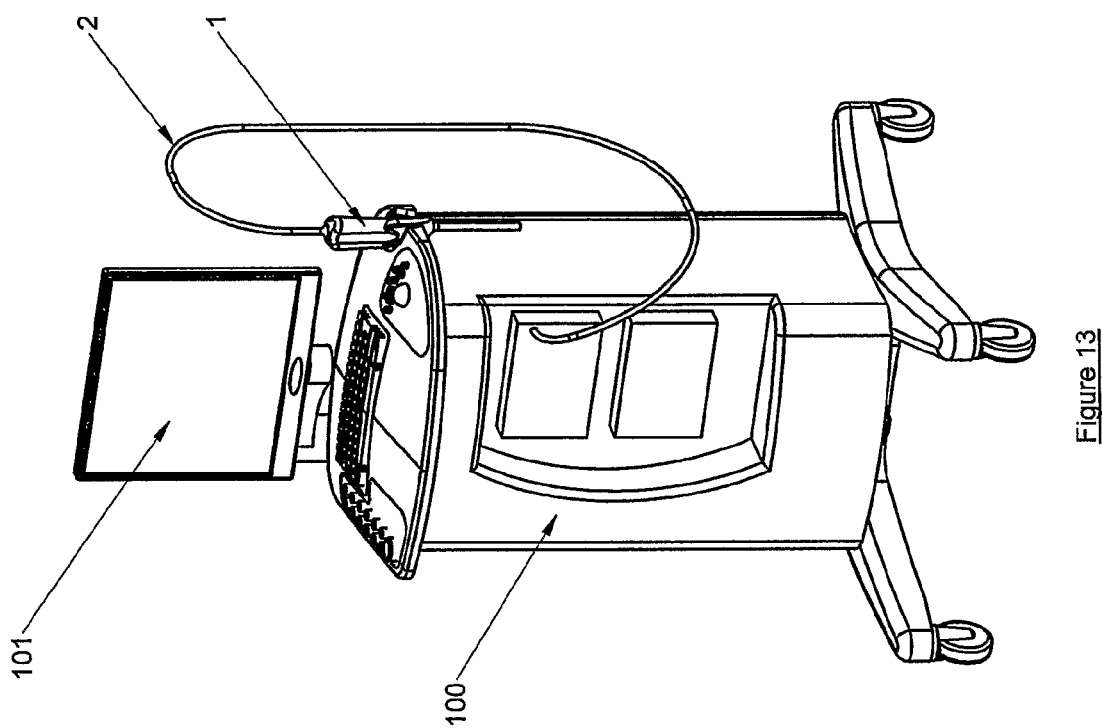
FIG. 13 shows a perspective view of an OCT apparatus according to one illustrated embodiment.

FIG. 13 shows a perspective view of the apparatus comprising a housing 100 mounting a computer system to analyze the interferograms and display the results on a screen 101. The housing 100 also mounts the laser, the output beam of which is passed to the probe 1 via the flexible single-mode optical fiber 2.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An optical interference apparatus for carrying out Fourier domain optical coherence tomography, comprising:
    a first beam splitter configured to generate a plurality of beams wherein interferograms are recorded simultaneously for a plurality of different focal depths within a substance to be examined, each interferogram being provided by one of the plurality of beams, the first beam splitter including:
  a reflecting surface; and
  a partially reflecting surface, wherein a received beam passes to the partially reflecting surface and a proportion of the beam passes through the partially reflecting surface to form a first beam and another proportion is reflected to the reflecting surface where it is reflected back to the partially reflecting surface and a proportion of the beam passes through the partially reflecting surface to form a second beam, the partially reflecting surface and the reflecting surface being disposed so that the first and second beam are displaced parallel to one another, further successive beams of the plurality of beams being provided by reflections and transmissions at the reflecting surface and the partially reflecting surface; and
  a probe configured to pass the plurality of beams to the substance to be examined at the plurality of different focal depths.

2. An optical interference apparatus as claimed in claim 1, further comprising at least one processor configured to combine images derived from said interferograms for a plurality of different focal depths, wherein a single image is constructed with an increased depth of field.

3. The optical interference apparatus of claim 1 wherein the probe is configured to provide a relevant measurement beam for each different focal depth.

4. An optical interference apparatus as claimed in claim 1 wherein foci of the plurality of beams are displaced both laterally and axially from one of the plurality of beams to a next one of the plurality of beams.

5. An optical interference apparatus as claimed in claim 1 wherein the first beam splitter comprises a rattle plate and said reflecting surface and partially reflecting surface are surfaces of the rattle plate, and wherein said received beam is a converging or diverging beam input to the rattle plate so that each of said plurality of beams from the rattle plate is brought to a different axial focus.

6. An optical interference apparatus as claimed in claim 1 wherein the plurality of beams consists of four beams.

7. An optical interference apparatus as claimed in claim 4 in which the axial spacing of the foci is based on a Rayleigh range of a focal waist in the substance to be examined.

8. An optical interference apparatus for carrying out Fourier domain optical coherence tomography, comprising:
  a rattle-plate beamsplitter assembly configured to provide multiple light beams, wherein more than one of the multiple light beams is operable to provide an interferogram such that the interferogram are simultaneously recorded for a plurality of different focal depths within a substance to be examined, the rattle-plate beamsplitter assembly including:
    a non-reflecting surface configured to receive a source light beam;
    a reflecting surface; and
    a partially reflecting surface;
  such that a received light beam passes to the partially reflecting surface, the partially reflecting surface allowing a proportion of the received light beam to pass through the partially reflecting surface to form a first light beam and reflecting another proportion of the received light beam to the reflecting surface where the another proportion of the received light beam is reflected back to the partially reflecting surface and a proportion of the reflected another proportion of the received light beam passes through the partially reflecting surface to form a second light beam, the partially reflecting surface and the reflecting surface being disposed so that the first and the second light beams are displaced substantially parallel to one another; and
  a probe configured to pass the more than one of the multiple light beams to the substance to be examined.

9. The optical interference apparatus as claimed in claim 8, further comprising:
  an image processing system configured to combine images derived from said interferograms corresponding to a plurality of different focal depths, wherein a single image may be constructed based on the combined images with an increased depth of field.

10. The optical interference apparatus as claimed in claim 8 wherein the probe is configured to provide a relevant measurement light beam for each different focal depth.

11. The optical interference apparatus as claimed in claim 8 wherein foci of the multiple light beams are displaced both laterally and axially from one another.

12. The optical interference apparatus as claimed in claim 8, wherein said reflecting surface and said partially reflecting surface comprise opposite surfaces of a rattle plate in the rattle-plate beamsplitter assembly, said rattle plate configured to
  have a converging or diverging light beam inputted to said rattle plate, and
  output said multiple light beams from the rattle plate such that each of the outputted multiple light beams is brought to a different axial focus.

13. The optical interference apparatus as claimed in claim 8 wherein the multiple light beams comprise four light beams.

14. The optical interference apparatus as claimed in claim 11 wherein an axial spacing of the foci is based on a Rayleigh range of focal waist in the substance to be examined.

15. The optical interference apparatus as claimed in claim 8, further comprising:
  a processing system including a processor configured to carry out Fourier domain optical coherence tomography.

16. The optical interference apparatus as claimed in claim 8, wherein the rattle-plate beamsplitter is further configured to provide further successive light beams of the multiple light beams by reflections and/or transmissions at the reflecting surface and the partially reflecting surface.

17. An optical interference apparatus for carrying out Fourier domain optical coherence tomography, comprising:
  a first beam splitter configured to generate a plurality of beams wherein interferograms are recorded simultaneously for a plurality of different focal depths within a substance to be examined, each interferogram being provided by one of the plurality of beams, the first beam splitter including:
    a reflecting surface; and
    a partially reflecting surface, wherein a received beam passes to the partially reflecting surface and a proportion of the beam passes through the partially reflecting surface to form a first beam and another proportion is reflected to the reflecting surface where it is reflected back to the partially reflecting surface and a proportion of the beam passes through the partially reflecting surface to form a second beam, the partially reflecting surface and the reflecting surface being disposed so that the first and second beam are displaced parallel to one another, further successive beams of the plurality of beams being provided by reflections and transmissions at the reflecting surface and the partially reflecting surface; and a scanner configured to scan the plurality of beams at right angles to the plurality of beams along a line which passes through the plurality of beams.

18. The optical interference apparatus of claim 17, further comprising at least one processor configured to combine images derived from said interferograms for a plurality of different focal depths, wherein a single image is constructed with an increased depth of field.

19. The optical interference apparatus of claim 17 wherein foci of the plurality of beams are displaced both laterally and axially from one of the plurality of beams to a next one of the plurality of beams.

20. The optical interference apparatus of claim 17 wherein the first beam splitter comprises a rattle plate and said reflecting surface and partially reflecting surface are surfaces of the rattle plate, and wherein said received beam is a converging or diverging beam input to the rattle plate so that each of said plurality of beams from the rattle plate is brought to a different axial focus.

21. The optical interference apparatus of claim 17, further comprising:
a probe configured to pass the plurality of beams to the substance to be examined.

22. An optical interference apparatus for carrying out Fourier domain optical coherence tomography, comprising:
a rattle-plate beamsplitter assembly configured to provide multiple light beams, wherein more than one of the multiple light beams is operable to provide an interferogram such that the interferogram are simultaneously recorded for a plurality of different focal depths within a substance to be examined, the rattle-plate beamsplitter assembly including:
a non-reflecting surface configured to receive a source light beam;
a reflecting surface; and
a partially reflecting surface, such that a received light beam passes to the partially reflecting surface, the partially reflecting surface allowing a proportion of the received light beam to pass through the partially reflecting surface to form a first light beam and reflecting another proportion of the received light beam to the reflecting surface where the another proportion of the received light beam is reflected back to the partially reflecting surface and a proportion of the reflected another proportion of the received light beam passes through the partially reflecting surface to form a second light beam, the partially reflecting surface and the reflecting surface being disposed so that the first and the second light beams are displaced substantially parallel to one another; and
a scanner configured to scan the multiple light beams at substantially right angles to the multiple light beams along a line which passes through the multiple light beams.

23. The optical interference apparatus of claim 22, further comprising:
an image processing system configured to combine images derived from said interferograms corresponding to a plurality of different focal depths, wherein a single image may be constructed based on the combined images with an increased depth of field.

24. The optical interference apparatus of claim 22 wherein foci of the multiple light beams are displaced both laterally and axially from one another.

25. The optical interference apparatus of claim 22, wherein said reflecting surface and said partially reflecting surface comprise opposite surfaces of a rattle plate in the rattle-plate beamsplitter assembly, said rattle plate configured to
have a converging or diverging light beam inputted to said rattle plate, and
output said multiple light beams from the rattle plate such that each of the outputted multiple light beams is brought to a different axial focus.

26. The optical interference apparatus of claim 22, further comprising:
a probe configured to pass the more than one of the multiple light beams to the substance to be examined.

* * * * *